(12) United States Patent
Nichols

(10) Patent No.: US 10,252,051 B2
(45) Date of Patent: *Apr. 9, 2019

(54) HANDHELD FACIAL MASSAGE AND LIGHT THERAPY DEVICE

(76) Inventor: Thomas Nichols, Laguna Niguel, CA (US)

( * ) Notice: Subject to any disclaimer, the term of this patent is extended or adjusted under 35 U.S.C. 154(b) by 925 days.

This patent is subject to a terminal disclaimer.

(21) Appl. No.: 13/592,226

(22) Filed: Aug. 22, 2012

(65) Prior Publication Data

US 2013/0046212 A1    Feb. 21, 2013

Related U.S. Application Data

(63) Continuation-in-part of application No. 13/173,439, filed on Jun. 30, 2011, now Pat. No. 9,272,141.

(Continued)

(51) Int. Cl.
*A61N 1/26* (2006.01)
*A61H 7/00* (2006.01)
*A61N 1/36* (2006.01)
*A46B 13/02* (2006.01)
*A61H 23/02* (2006.01)
*A61N 1/00* (2006.01)
*A61N 1/32* (2006.01)

(Continued)

(52) U.S. Cl.
CPC .......... *A61N 1/36014* (2013.01); *A46B 7/04* (2013.01); *A46B 13/008* (2013.01); *A46B 13/023* (2013.01); *A46B 15/0034* (2013.01); *A61H 7/005* (2013.01); *A61H 23/0263* (2013.01); *A61N 1/00* (2013.01); *A61N 1/0404* (2013.01); *A61N 1/322* (2013.01);
*A61N 1/328* (2013.01); *A46B 2200/102* (2013.01); *A61H 2201/10* (2013.01); *A61H 2201/1685* (2013.01); *A61H 2205/022* (2013.01)

(58) Field of Classification Search
CPC .... A61N 1/00; A61N 1/36014; A61N 1/0404; A61N 1/328; A46B 13/008; A46B 13/023; A46B 7/04; A61H 23/0263; A61H 7/005
See application file for complete search history.

(56) References Cited

U.S. PATENT DOCUMENTS 6,026,828 A     2/2000  Altshuler .................. 132/311
6,443,915 B1 *  9/2002  Hwang ...................... 601/15
(Continued)

*Primary Examiner* — Justine Yu
*Assistant Examiner* — Timothy Stanis
(74) *Attorney, Agent, or Firm* — Knobbe Martens Olson & Bear LLP

(57) ABSTRACT

One form of the device is a standard handpiece having a series of interchangeable treatment heads. The handpiece can accept cooperating treatment heads for twist-locking therein or by other engagement arrangement. The treatment heads may or may not have an internal motor assembly within them to create vibratory motion in the assembled device. The groups of possible treatment heads include LED-light-emitting heads, microcurrent-emitting heads, a treatment head having an abrasive or pebbled surface, as well as a bristle brush head. In another version, the handpiece and treatment head are integrated and not exchangeable. In this second version, a combination LED-light-emitting outer ring surrounds a central dual-lobe massage surface. The dual-lobe massage surface may be made from an inert material such as silicone, or it may be metallic in order to provide emission of therapeutic microcurrents.

17 Claims, 10 Drawing Sheets

Related U.S. Application Data

(60) Provisional application No. 61/360,826, filed on Jul. 1, 2010.

(51) Int. Cl.
*A61N 1/04* (2006.01)
*A46B 7/04* (2006.01)
*A46B 13/00* (2006.01)
*A46B 15/00* (2006.01)

(56) References Cited

U.S. PATENT DOCUMENTS

| | | |
|---|---|---|
| 7,384,405 B2 | 6/2008 | Rhoades .................. 601/15 |
| 7,748,070 B2 | 7/2010 | Chan et al. .................. 15/22.1 |
| 2005/0075149 A1* | 4/2005 | Gerber et al. ............ 455/575.1 |
| 2006/0058714 A1 | 3/2006 | Rhoades .................. 601/73 |
| 2006/0253051 A1* | 11/2006 | Milne et al. .................. 601/15 |
| 2007/0123808 A1 | 5/2007 | Rhoades .................. 601/73 |
| 2008/0119913 A1* | 5/2008 | Powell et al. .................. 607/88 |
| 2008/0243039 A1 | 10/2008 | Rhoades .................. 601/73 |
| 2009/0177125 A1 | 7/2009 | Pilcher et al. .................. 601/18 |
| 2009/0312691 A1* | 12/2009 | Kim et al. .................. 604/22 |
| 2010/0049177 A1* | 2/2010 | Boone et al. .................. 606/9 |
| 2010/0121419 A1* | 5/2010 | Douglas .................. 607/90 |
| 2010/0210993 A1* | 8/2010 | Flyash et al. .................. 604/20 |
| 2010/0292746 A1* | 11/2010 | Gorham .................. 607/3 |
| 2011/0098781 A1* | 4/2011 | Mantle et al. .................. 607/46 |
| 2011/0106067 A1* | 5/2011 | Geva et al. .................. 606/9 |
| 2011/0184499 A1 | 7/2011 | Radi .................. 607/88 |

* cited by examiner

HANDHELD FACIAL MASSAGE AND LIGHT THERAPY DEVICE

This application is a continuation-in-part of application Ser. No. 13/173,439, filed Jun. 30, 2011, now U.S. Pat. No. 9,272,141, and claims priority to the relevant disclosure from Provisional Patent Application Ser. No. 61/360,826, filed Jul. 1, 2010 (both collectively referred hereinafter to as the "Parent Application").

BACKGROUND OF THE INVENTION

1. Field of the Invention

This invention relates generally to facial treatment apparatus and, more specifically, to a Handheld Facial Massage and Light Therapy Device.

2. Description of Related Art

Handheld facial treatment devices for home use have become a very active field of invention recently. A plurality of new devices each, in their own way, seek to give a consumer the ability to self-administer many skin treatments that were previously only available in a medical office environment. In particular, the use of LED light in particular wavelengths, and the incorporation of motorized massaging features have been quite popular.

The device that is the subject of U.S. Pat. No. 7,384,405 to Rhoades combines a facial brush/applicator with an internal mechanism for generating vibration. While the Rhoades patent does disclose a device having interchangeable massage heads, it does not suggest the use of either light therapy or microcurrent therapy.

Chan, et al, U.S. Pat. No. 7,748,070 is a motorized toothbrush that also emits LED light—allegedly to kill microorganisms on the user's teeth. While the Chan device does suggest the use of exchangeable brush elements, there is no disclosure of the emission of microcurrents for skin treatment (this is not a skin treatment device), nor are the LED light elements exchangeable to provide different color treatments. Furthermore, there is no motorized mechanism in the Chan device to create vibration in the treatment head for the purpose of massaging the skin.

A final relevant device is the subject of U.S. Patent Application Publication No. 2009/0240310 filed by Kennedy. The Kennedy device is a handheld facial skin treatment device having interchangeable LED light treatment heads available in a variety of shapes. The Kennedy device further does incorporate an internal "sonic" vibration mechanism within the handpiece. The Kennedy device does not, however, suggest the providing of microcurrents through the treatment head, nor does it suggest the positioning of the vibration generator within the interchangeable treatment head, rather than within the handpiece. The distinction being that if the vibration generator is always a part of the unit, then the added weight will also be carried by the user. If it is moved to the interchangeable head module, then the basic handpiece will be much lighter and less complex in nature, and therefore likely to be more useful to users in a wider variety of treatment configurations.

SUMMARY OF THE INVENTION

In light of the aforementioned problems associated with the prior devices and systems, it is an object of the present invention to provide a Handheld Facial Massage and Light Therapy Device. One form of the device is a standard handpiece having a series of interchangeable treatment heads insertible therein. The handpiece should have a head receptacle for accepting cooperating treatment heads for twist-locking therein. The treatment heads may or may not have an internal motor assembly within them to create vibratory motion in the assembled device. The treatment heads should include LED-light-emitting heads, microcurrent-emitting heads, a treatment head having an abrasive or pebbled surface, as well as a bristle brush head. Other versions of the treatment head may combine the features of the aforementioned heads. In another version, the handpiece and treatment head should be integrated and not exchangeable. In this second version, a combination LED-light-emitting outer ring should surround a central dual-lobe massage surface. The dual-lobe massage surface may be made from an inert material such as silicone, or it may be metallic in order to provide emission of therapeutic microcurrents.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a Handheld Facial Massage and Light Therapy Device.

Figure 1:
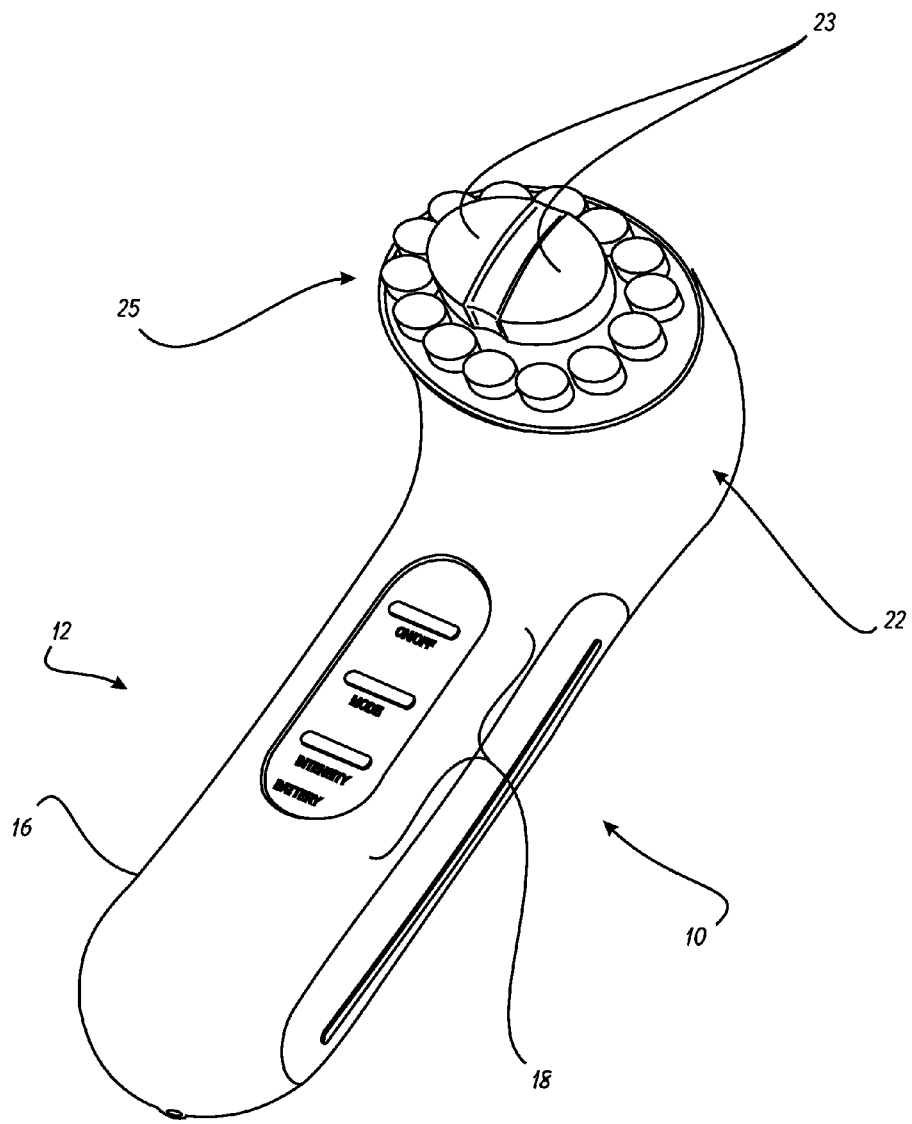
FIG. 1 is a perspective view of a preferred embodiment of the present invention having a combination current emitter face and LED light ring.

The present invention can best be understood by initial consideration of FIG. 1. FIG. 1 is a perspective view of a preferred embodiment of the present invention having a combination current emitter face and LED light ring. This version 10 combines the therapeutic benefits of two different technologies—microcurrent skin therapy as well as rejuvenation by light therapy. The handheld massage device 10 has a handpiece 12 that is further defined by a head portion 22 and a handle portion 16. This device 10 is, in fact, very similar in some ways to the device that is the subject of the Parent Application. The critical difference being the incorporation of the LED light ring 25 encircling the current emitter face 23.

The LED lamps that comprise the light ring 25 could be blue (approximately 415 nm wavelength) for treatment of acne in the skin, or they could be red (wavelength approximately 660 nm) in order to treat skin wrinkles. The ring 25 may be permanently attached to the head portion 22, or it may be interchangeable with other rings 25 (such as in alternate colors even beyond blue or red).

The current emitter face 23 serves to transmit microcurrents into the skin in order to rejuvenate and stimulate collagen production. The disclosure of such functionality and benefits is fully described in the Parent Application and is incorporated herein by reference.

The mode control switch 18 dispersed on the handle section 16 of the handpiece 12 is used to operate the microcurrent and light emission features. There may further be lamps adjacent to the touch-sensitive switches in order to display the current device operational status. These features are also fully disclosed by the Parent Application. An alternate embodiment of the device 10 of the present invention is depicted in FIG. 2.

Figures 2A, 2B:
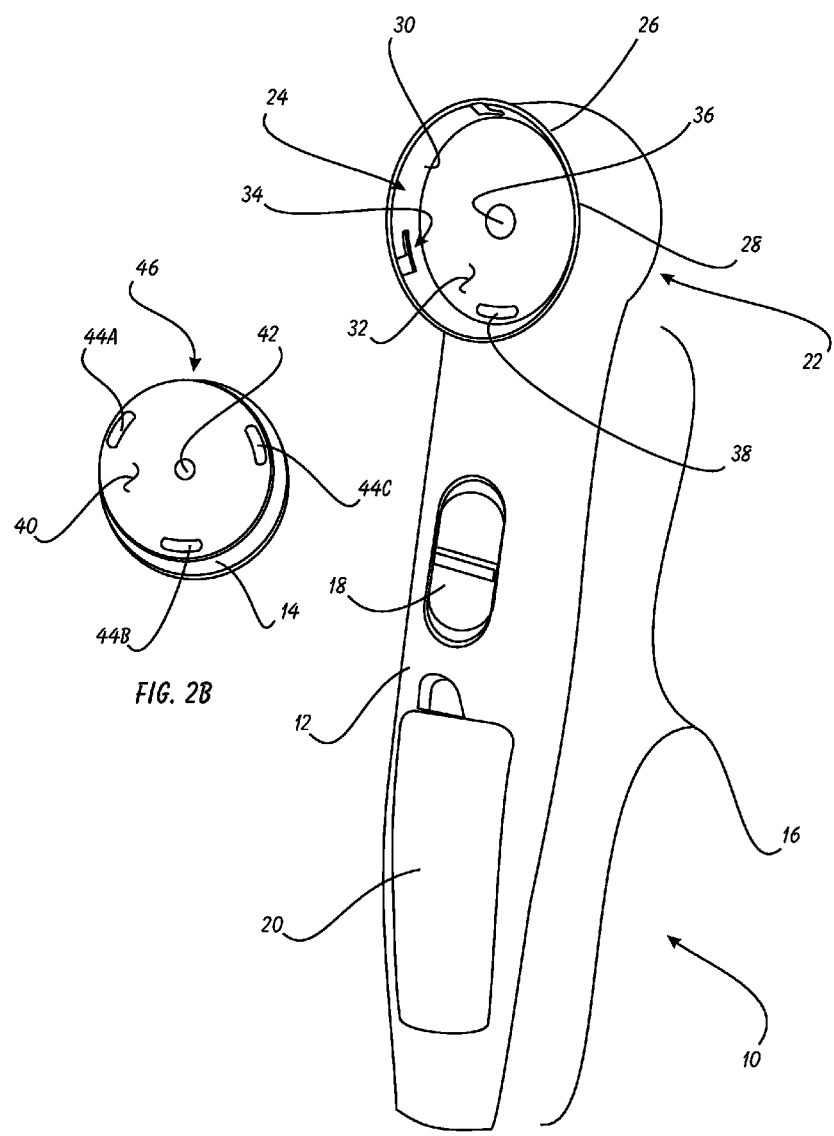
FIG. 2A is a partially exploded perspective view of a version of the device of FIG. 1.
FIG. 2B is a rear perspective view of an interchangeable head module.

FIG. 2 is a partially exploded perspective view of a version of the device 10 of FIG. 1, having a interchangeable head module 14. The handheld massage device 10 depicted here has a handpiece 12 defined by a handle portion 16 and head portion 22. A mode control switch 18 is disposed on the handle portion 16, and access to internal batteries (preferably two AA size rechargeable batteries, but could also be non-rechargeable batteries) is provided by the battery cover 20.

A significant difference between the device of FIG. 1 and that of FIG. 2 is related to the structure of the head portion 22 and head module 14. Rather than featuring an integrated skin treatment head, the version of the device 10 depicted here is designed to allow the user to take advantage of a wide variety of skin treatment technologies while using a single handpiece 12. This functionality is provided by the use of a group of compatible, interchangeable head modules 14—different head modules 14 can be attached to the head portion 22 to provide a variety of different skin treatment technologies to the user.

The head portion 22 is formed with a head receptacle 24 formed within it. The head receptacle 22 is, essentially, a recessed portion formed in the head portion 22 of the handpiece 12 that will accept a cooperatively-sized head module 14. The receptacle 24 is defined by a generally circular sidewall 30 terminating in a substantially flat rear face 32.

The sidewall terminates at its outermost edge in the smooth rim 28 to define the head opening 26 into which the head module 14 is inserted (at least partially). The sidewall 30 may be slightly conical in shape in order to make it easier to insert and remove head modules 14 (i.e. to prevent binding).

In order to avail electric power for use by the head module 14, at least one pair of electrical contact pads (one positive and one negative in polarity) are provided within the head receptacle 24 for interconnection with suitably located corresponding pads on the head module 14. In the depicted device version, there is a center contact pad 36 centralized on the rear face 32 of the receptacle 24. At least one perimeter contact pad 38 is towards the outer periphery of the circular rear face 32, and is generally expected to be shaped in a somewhat arcuate form.

A plurality of interlock grooves 34 are provided around the periphery of the sidewall 30 adjacent to the rim 28. These generally "L"-shaped grooves 34 are designed to engage interlock ridges [e.g. 74A][1] dispersed on the outer periphery of the inner housing portion [e.g. 46A] so that the head module(s) can be twist-locked into engagement with the head receptacle 24 to prevent its inadvertent disengagement, and further to ensure positive electrical contact with the contact pads 36, 38. The head module 14 will also twist-unlock.

[1] Square brackets [ ] are utilized herein to denote that the identified element contained with the square brackets is not found in the context of the particular drawing figure being discussed, but rather is found elsewhere in the Disclosure and in another drawing figure.

The head module 14 is defined in part by an inner housing portion 46 that terminates at its end in internal face 40. There is a center contact pad 42 and two or more perimeter contact pads 44A, 44B, 44C (three pads here) dispersed on the internal face 40. The three pads 44A-44C correspond to their being three interlock grooves 34 (and ridges [e.g. 74A]) on the sidewall 30 and inner housing portion 46, respectively—there are three possible relative angular positions between the head module 14 and head receptacle 24 for engagement between the two. Providing three separate pads 44A-44C ensures that at least one of the pads 44A-44C will engage the perimeter contact pad 38, no matter what the relative angular orientation is between the head receptacle 24 and the head module 14. Now turning to FIG. 3, we will commence examination of some of the potential configurations and treatments afforded by the system of the present invention.

Figure 3:
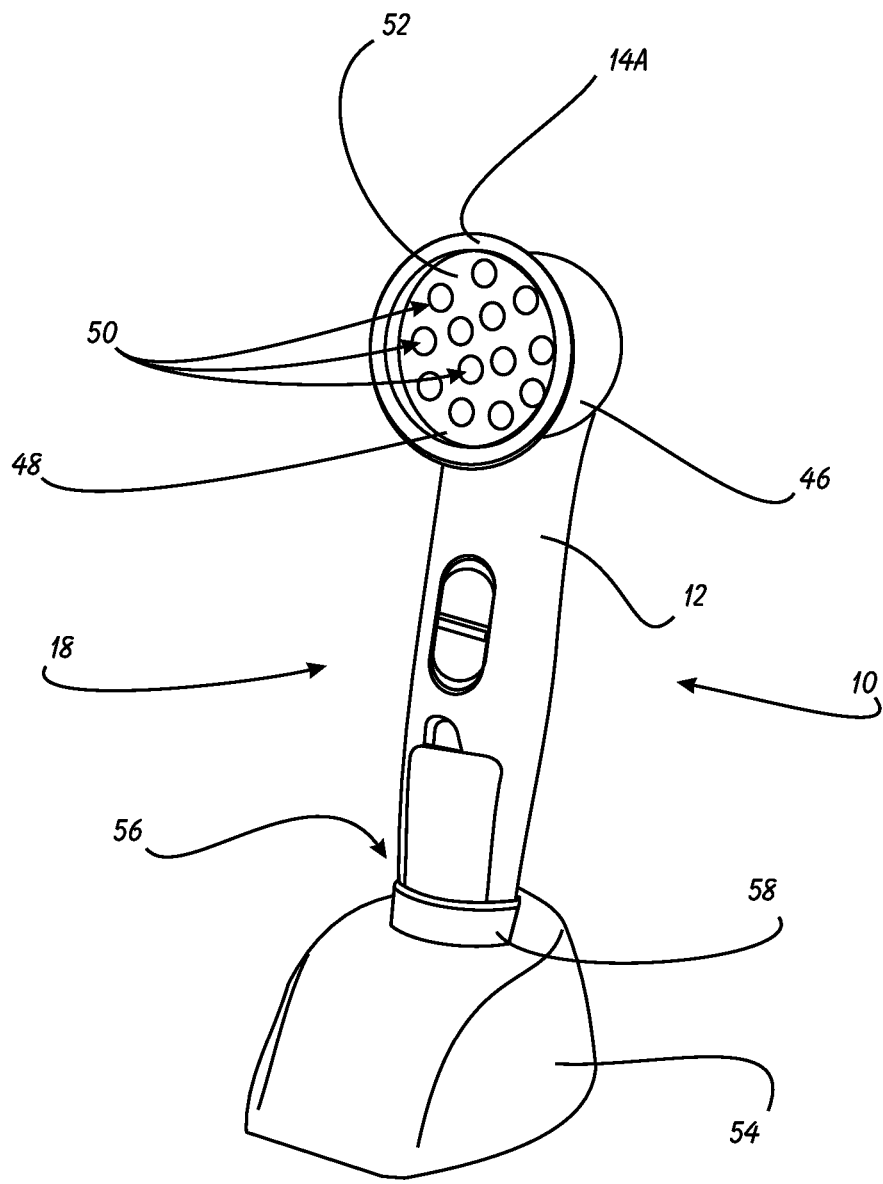
FIG. 3 is a perspective view of the device of FIG. 2 having an LED light head module installed therein.

FIG. 3 is a perspective view of the device 10 of FIG. 2 having an LED light head module 14A installed therein. In this view, the handpiece 12 has been placed into the charging receptacle 56 formed in the charging base 54. As should be apparent, the charging base 54 connects to a conventional electrical power source to provide power to recharge the batteries contained within the handpiece 12. In this version the receptacle 56 is fitted with a stabilizing sleeve 58. The stabilizing sleeve 58 serves to reduce the diameter of the receptacle 56 in order to accommodate a handpiece 12 having a thinner profile than the base 54 was created to accommodate. The sleeve 58, then, allows the user to use a single charging base 54 for handpieces 12 having a variety of different diameters.

Figure 4:
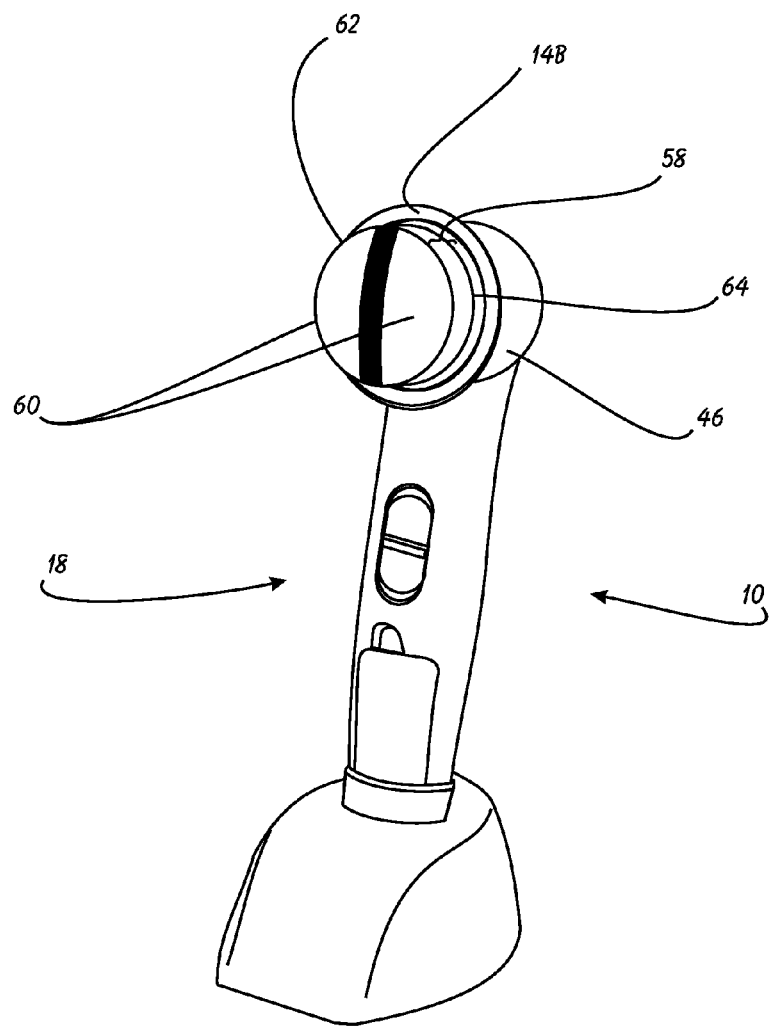
FIG. 4 is a perspective view of the device of FIGS. 2 and 3 having a dual-lobe massage face head module installed therein.

The LED light head module 14A has a head module housing 46 defined by an opening at its front side. The opening is covered by a lens 48 (typically clear) to form an internal chamber. Within the internal chamber (which is sealed from intrusion of liquid at its front) is a lamp substrate 52 from which protrude a plurality of LED light elements 50. These light elements 50 are preferably of a single color (e.g. blue or red), however, since the LED light head module 14A is interchangeable with other head modules, a user may have one blue light module 14A and one red light module 14A. FIG. 4 depicts yet another conversion device made available through the present design.

FIG. 4 is a perspective view of the device 10 of FIGS. 2 and 3 having a dual-lobe massage face head module 14B installed therein. The dual-lobe massage head 14B may be configured in two ways—one is strictly for vibrating massage, and is fitted with a silicone-coated face; the other has the current emitter structure and functionality as discussed in the Parent Application and in FIG. 1, and will provide both vibrating massage and microcurrent skin therapy to the user's skin.

The dual-lobe massage head module 14B has a dual-lobed face 60 protruding from the head housing 46. There is an insulation element 62 sandwiched between the two lobes comprising the face 60. As should be apparent, the sidewall 64 of the current emitter element 58 terminating in the face 60 will be metallic when of the type that emanates microcurrents, and will be non-metallic (typically) when the simple vibratory massage version of head module 14B. The mode control switch 18 will control the operation of the vibration and (if so-equipped) microcurrent emission of the device 10. These two devices 10A and 10B are more fully disclosed in connection with FIG. 5.

Figure 5:
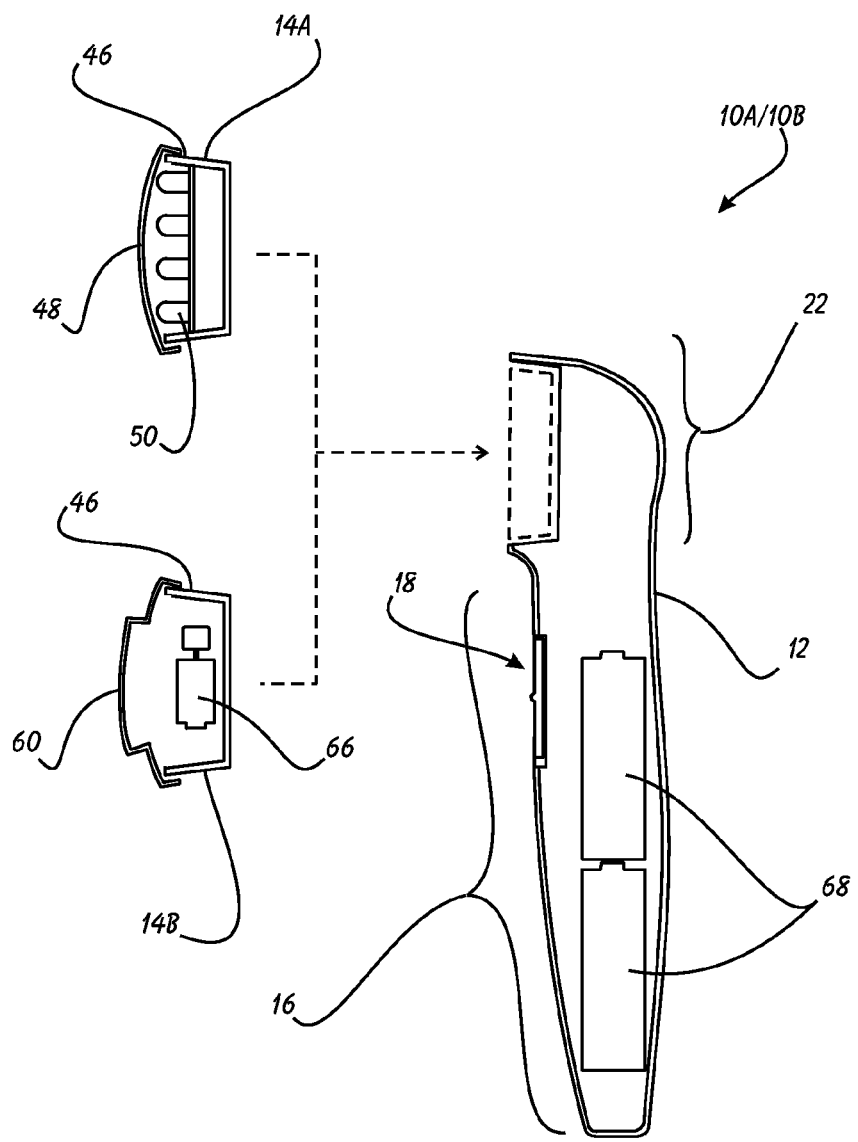
FIG. 5 is an exploded cutaway side view of the device of FIGS. 2-4 and the head modules of FIGS. 3 and 4.

FIG. 5 is an exploded cutaway side view of the device 10 of FIGS. 2-4 and the head modules 14A/14B of FIGS. 3 and 4. As discussed above, a pair of batteries 68 is contained within the handle portion 16 of the handpiece 12. The head receptacle 24 is a recessed pocket formed within the head portion 22.

Figure 6:
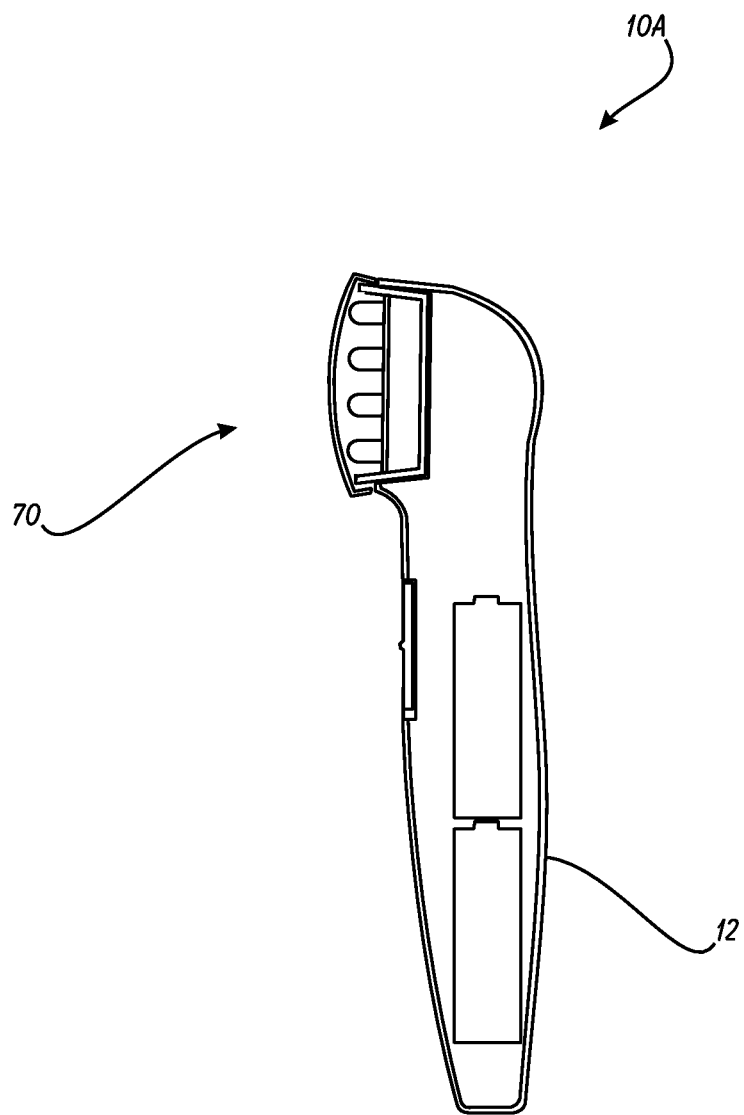
FIG. 6 is a cutaway side view of the device of FIG. 3.
Figure 7:
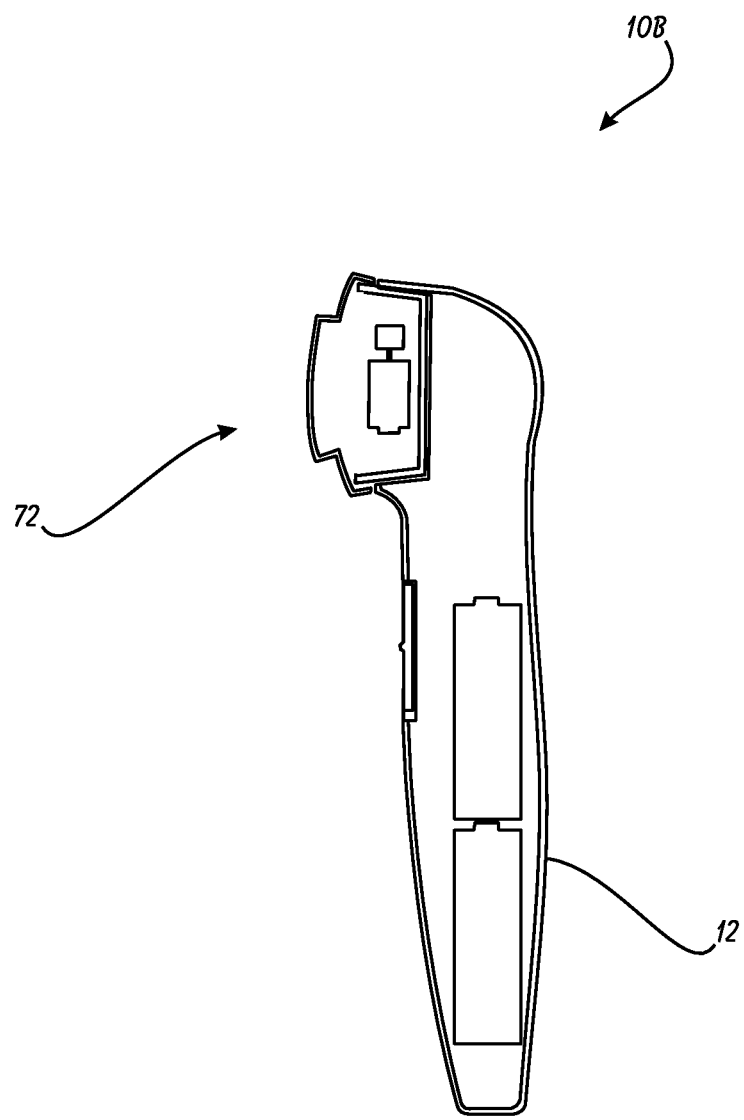
FIG. 7 is a cutaway side view of the device of FIG. 4.

The LED light head module 14A has a plurality of LED light elements 50 within the head housing 46 and positioned behind the lens 48. The massage head module 14B (whether current-emitting or not) has an internal mechanism for generating vibrations in the head module 14B (and head portion 22 when the module 14B is locked into the handpiece 12). The mode control switch 18 will only operate the functions of either head module 14A, 14B when that module is locked into the head receptacle 24 so that the contact pads [36, 38, 42 and 44A-4C] are appropriately connected to create an electrical connection therethrough. FIGS. 6 and 7 show the device 10 in its fully assembled state.

FIG. 6 is a cutaway side view of the device 10A of FIG. 3 and FIG. 7 is a cutaway side view of the device 10B of FIG. 4. The light-emitting massage device 10A is the result of the LED light head module [14A] being interlocked to the handpiece 12. The result is indistinguishable to the user (in terms of functionality) from a non-interchangeable device, and can be presented in either form according to the present invention. The LED light emitter 70 generates and emits a selected color in order to provide the desired wavelength to treat a specific skin condition.

Similarly, the vibrating massage device 10B is the result of the massage head module [14B] into the handpiece 12 to provide the functionality of an integrated vibrating massage device having a vibrating massager head 72 for placement against the user's skin. The massage head module 14B is described in more detail in connection with FIG. 8.

Figure 8:
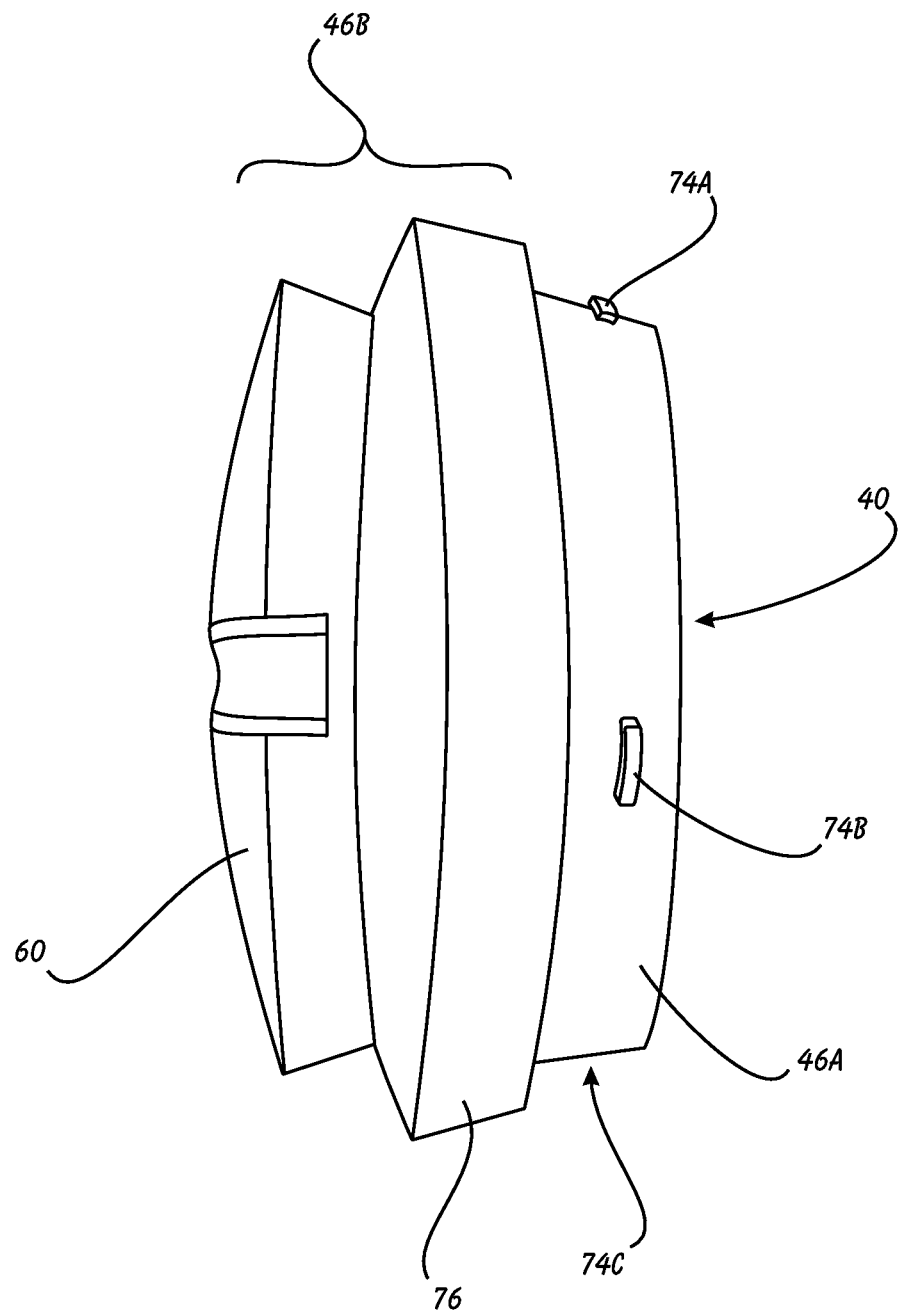
FIG. 8 is a side view of the dual-lobe massage face head module of FIG. 4.

FIG. 8 is a side view of the dual-lobe massage face head module 14B of FIG. 4. It is noted that the features described herein related to the inner housing portion 46A are identical for each and every head module 14 described or suggested in the instant Specification; it is only the outer housing portion 46B that changes from module to module.

The massage head module 14B has a somewhat conical inner housing portion 46A that terminates at its innermost end in the internal face 40 (whereat the contact pads are dispersed). There are three interlock ridges 74A, 74B and 74C (not shown) protruding outwardly from the inner housing portion 46A. These ridges 74A-74C are designed to cooperate with the interlock grooves [34] to create the twist-lock feature provided by the device 10.

Figure 9:
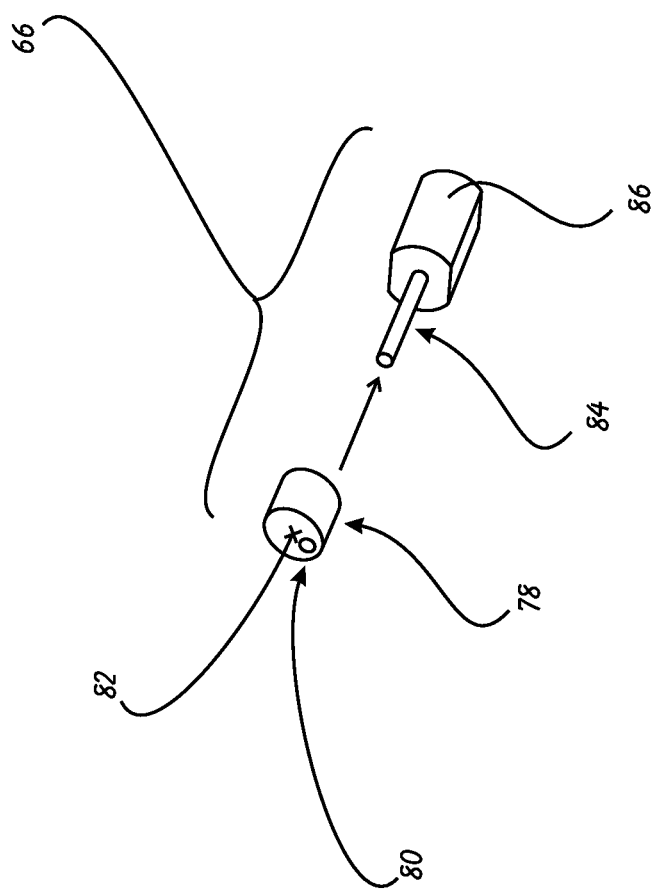
FIG. 9 is an exploded perspective view of the motor subassembly of the head module of FIG. 4.

The outer housing portion 46B, in this case, terminates at its outer end in the dual-lobed massage face 60, which could be of the silicone-coated or the metallic type (for microcurrent emissions). The collar 76 is designed to preferably overlap the rim [28] in order to prevent foreign materials from contaminating the head receptacle [24] or inner housing portion 46A, such as with lotions or other liquids. FIG. 9 depicts the final element of the instant design not yet discussed.

FIG. 9 is an exploded perspective view of the motor subassembly 66 of the head module [14B] of FIG. 4. As was first disclosed in the Parent Application, the vibrations generated by the massage head module [14B] are the result of a weight element rotating out of balance. The offset weight element 78 has a shaft bore 80 in spaced relation to the geometric center axis 82. The offset weight element 78 is mounted to the motor shaft 84 at the shaft bore 80. Since the center of rotation of the motor 86 will be in spaced relation to the center of mass of the weight element 78, the subassembly 66 will cause shaking or vibration when the motor drives the shaft 84 and weight element 78 to rotate. As noted earlier, in the present invention, the motor subassembly 66 is a component of the head module rather than of the handpiece. As a result, the vibrating feature will only be provided when the particular head module installed within the handpiece contains the motor subassembly 66. If we finally turn to FIG. 10, we can see the expandability achieved by the design of this novel device and system.

Figure 10:
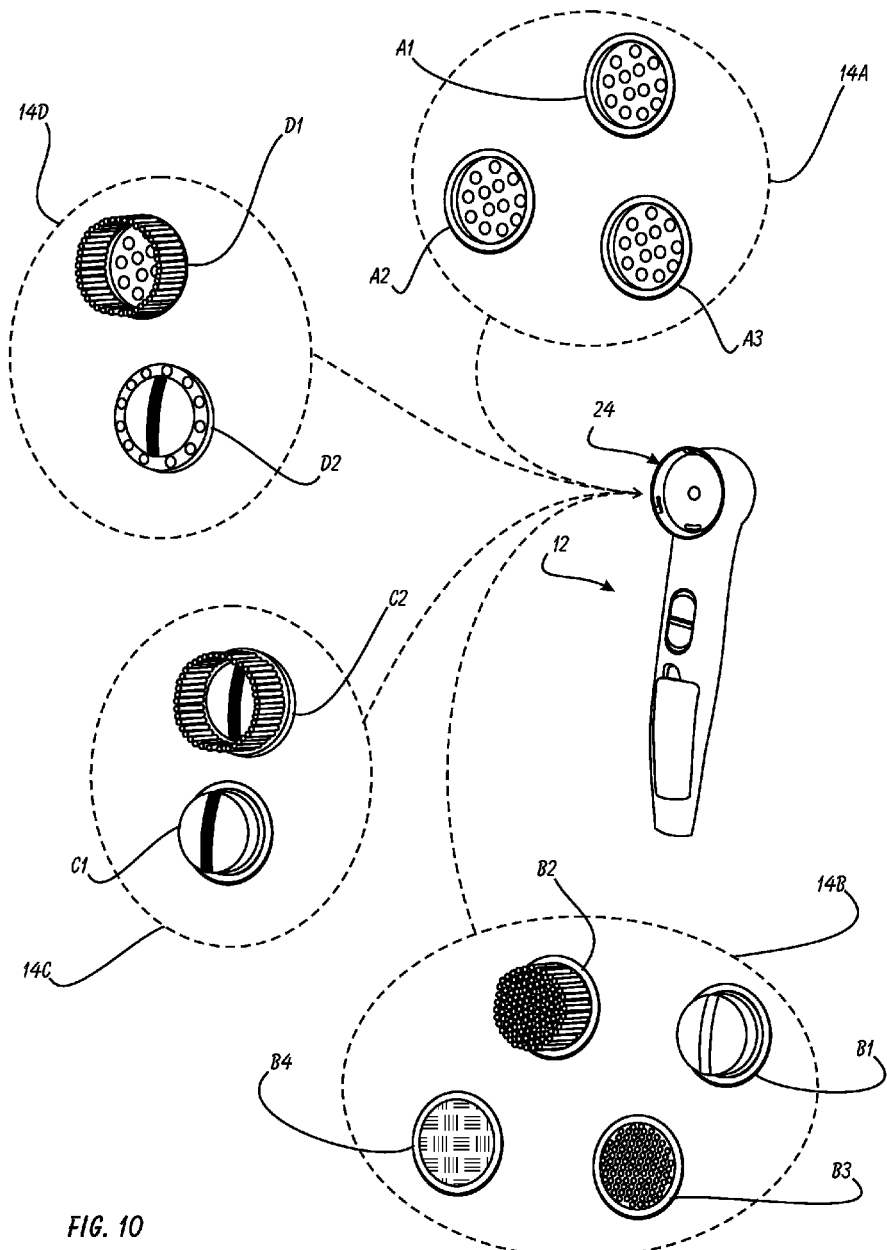
FIG. 10 depicts the device of the present invention along with examples of the wide variety of head modules compatible therewith.

FIG. 10 depicts the device of the present invention along with examples of the wide variety of head modules compatible therewith. As discussed previously, a major strength of the device of the present invention is that a single handpiece is compatible with any head module that will fit within the head receptacle 24. While not exclusive, the following possible combinations are contemplated by the inventor:

14A—Group I—"LED light modules":
A1 is a red LED light module;
A2 is a blue LED light module; and
A3 is a green LED light module.
White and other colors would naturally be available in other separate light modules.

14B—Group II—"Massage head modules"—each head module having the internal motor subassembly for creating vibratory motion:
B1 is a dual-lobed massage face having the smooth, preferably silicone-coated face;
B2 has brush bristles for brushing the skin using vibratory motion;
B3 has a material that is somewhat abrasive to the skin on its face, such as to exfoliate or smooth the skin using vibratory motion; and
B4 has a face with a "pebbled" surface for kneading the skin using vibratory motion.

14C—Group III—"Microcurrent head modules" These head modules may also include the motor subassembly for generating vibrations
C1 is the device discussed herein as the microcurrent emitting dual-lobed head module; and
C2 is a combination of the dual-lobed microcurrent emitting face, also having a bristle brush encompassing the emitter face—with the pebbled and abrasive versions being included in this C2 combination. As such, the microcurrent emitter face is one treatment surface, and the bristle brush defines an outer peripheral skin treatment surface.

14D—Group IV—combines the features of the LED light head modules with and without the vibration feature:
D1 has a plurality of brush bristles surrounding a central LED light emitter—with the pebbled and abrasive versions being included in this D1 combination; and
D2 has a central microcurrent generator encircled by a ring of LED lights. As such, the microcurrent emitter face is one treatment surface, and the ring of LED lights defines an outer peripheral skin treatment surface.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A facial treatment assembly combination, comprising:
a handpiece defined by a handle section and a head section extending therefrom, said head section further defined by a head receptacle formed therein and two or more electrical contact pads dispersed within the walls comprising said head receptacle;
a group of head modules, wherein one of said group of head modules is at least partially insertible into said head receptacle at a time, the group of head modules comprising at least:
a first light-emitting head module comprising a head module housing having one or more lamp elements contained therein, said first light-emitting module having a lens at a head module face such that said lamp elements are visible therethrough, the light emittable from said first light-emitting head module being of a first wavelength; and
a dual-lobed head module comprising a head module housing having a face from which extend a pair of face sections separated by a groove formed therebetween, said face sections further comprising an emitter element extending directly from said head module housing whereby said emitter face is defined by a pair of metallic elements each terminating in a metallic face, said metallic faces separated by a non-metallic insulation element, wherein said insulation element defines a groove that is recessed relative to said metallic faces; and
wherein each said head module further comprises two or more electrical contact pads dispersed on the wall defined by an inner housing portion of each said head module, said head module electrical contact pads cooperating with said handpiece electrical contact pads such that each said head module contact pads is aligned with a said handpiece contact pad when said head module is inserted into said head receptacle.

2. The assembly combination of claim 1, wherein each said face section is coated with an electrically-conductive material and said groove comprises an insulation element.

3. The assembly combination of claim 2, wherein said dual-lobed head module further comprises a peripheral portion substantially surrounding said pair of face sections, said peripheral portion further comprising one or more lamp elements visible through a lens attached thereto.

4. The assembly combination of claim 1, wherein said dual-lobed head module further comprises a peripheral portion substantially surrounding said pair of face sections, said peripheral portion further comprising one or more lamp elements attached thereto.

5. The assembly combination of claim 1, wherein said dual-lobed head module further comprises an internal motor subassembly, said internal motor subassembly configured to selectively generate mechanical vibration responsive to activating electrical power through said contact pads from said handpiece.

6. The assembly combination of claim 5, wherein said internal motor subassembly comprises:

an electric motor connectable to said electrical power;
a shaft extending from said motor, said shaft driven to rotate by said electric motor; and;
an offset weight element attached to a distal end of said shaft at a shaft bore, said shaft bore in spaced relation to a center axis of geometry of said offset weight element.

7. The assembly combination of claim 1 wherein said dual-lobed head module further comprises a peripheral portion substantially surrounding said pair of face sections, said peripheral portion further comprising a skin treatment surface section defined by a base attachable to said head module housing and a central aperture through which said pair of face sections protrude therethrough such that said emitter face is in spaced relation to said peripheral base, and said emitter element sidewall is adjacent to said skin treatment surface section.

8. The assembly combination of claim 7 wherein said peripheral portion skin treatment section comprises a plurality of brush bristles extending from said skin treatment surface section.

9. The assembly combination of claim 7, wherein:
said face sections define a first surface texture; and
said peripheral portion skin treatment section defines a second surface texture, said second surface texture being less smooth than said first surface texture.

10. The assembly combination of claim 9, wherein said second surface comprises a plurality of protrusions extending upwardly from said skin treatment section.

11. A facial treatment device, comprising:
a handpiece defined by a handle section and a head section;
a facial massage treatment assembly defined by a face protruding from said head section, said facial massage face comprising:
a first housing that detachably attaches to said head section;
a central current emitter section comprising a pair of metallic lobes in relative spaced relation and separated by an insulation element further comprising an emitter element extending directly from said first housing whereby said emitter face is defined by a pair of metallic elements each terminating in a metallic face, said metallic faces separated by a non-metallic insulation element, wherein said insulation element defines a groove that is recessed relative to said metallic faces;
a light emitting ring encompassing said central current emitter section; and
a mode control switch for activating said current emitter section to emit electrical current through said metallic lobes and further to activate said light emitting ring to emit colored light therefrom; and
said facial treatment device further comprising a second facial massage treatment assembly defined by a second housing detachably attachable to said head section, and
a vibration-generating mechanism contained within said second housing, with electrical current for said vibration-generating mechanism provided from said handle section.

12. The device of claim 11, wherein said handpiece further comprises an internal motor subassembly located in said first housing, said internal motor subassembly configured to selectively generate mechanical vibration responsive to activating electrical power through said mode control switch.

13. The device of claim 12, wherein said internal motor subassembly comprises:
- an electric motor connectable to said electrical power;
- a shaft extending from said motor, said shaft driven to rotate by said electric motor; and;
- an offset weight element attached to a distal end of said shaft at a shaft bore, said shaft bore in spaced relation to a center axis of geometry of said offset weight element.

14. A facial treatment assembly comprising:
- a handpiece defined by a handle section and a head section extending therefrom, said head section further defined by a head receptacle formed therein; and
- a group of head modules, wherein one of said group of head modules is at least partially insertible into said head receptacle at a time, the group of head modules comprising at least:
  - a dual-lobed head module comprising a head module housing having a face from which extend a pair of face sections separated by a groove formed therebetween, said face sections further comprising an emitter element extending directly from said head module housing whereby said emitter face is defined by a pair of metallic elements each terminating in a metallic face, said metallic faces separated by a non-metallic insulation element, wherein said insulation element defines a groove that is recessed relative to said metallic faces;
  - a vibrating head module comprising a head module housing defined by a massage face and an internal motor subassembly, said internal motor subassembly activatable from said handpiece to generate vibrations in said head module; and
  - a light-emitting head module comprising a head module housing having one or more lamp elements contained therein, said module further comprising a lens attached to said head module housing such that said lamp elements are visible therethrough.

15. The facial treatment assembly of claim 14, wherein:
- said head receptacle is defined by a head opening in said head section, said head receptacle comprises a peripheral sidewall encircling said head opening and terminating at a rim, said rim defining a rim diameter; and
- each said head module is defined by an inner housing portion and an outer housing portion, said inner housing portion configured to be insertible through said head opening whereby sidewalls defined by said head module are in close proximity with said head receptacle peripheral sidewall.

16. The facial treatment assembly of claim 15, wherein said head receptacle further comprises a plurality of contact pads dispersed on said sidewall or a rear face of said head receptacle; and
- each said head module further comprises a plurality of contact pads dispersed on said head module sidewall or an internal face defined by said head module.

17. The facial treatment assembly of claim 16, wherein said head receptacle further comprises one or more interlock grooves formed in said sidewall and each said head module comprises a corresponding number of ridges extending from said head module sidewall, said ridges interlocking with said grooves to secure each said head module within said head receptacle.

* * * * *